United States Patent [19]

Beck et al.

[11] Patent Number: 4,778,935
[45] Date of Patent: Oct. 18, 1988

[54] FLUORINATED NITRO- AND AMINOALCOHOLS

[75] Inventors: Albert K. Beck; Dieter Seebach, both of Zuerich, Switzerland

[73] Assignee: Bayer Aktiengesellschaft, Leverkusen, Fed. Rep. of Germany

[21] Appl. No.: 928,229

[22] Filed: Nov. 6, 1986

[30] Foreign Application Priority Data

Nov. 14, 1985 [DE] Fed. Rep. of Germany ....... 3540332

[51] Int. Cl.$^4$ ..................... C07C 79/18; C07C 79/20; C07C 79/22
[52] U.S. Cl. ................................... 568/705; 568/713; 549/445
[58] Field of Search ............... 568/588, 589, 705, 713, 568/705, 713; 558/423, 451; 549/445

[56] References Cited

PUBLICATIONS

Seeback, D. et al., *Angewandte Chemie,* vol. 25, No. 1, pp. 98–99 (1986).
Knunyants, I. L. et al., *Chemical Abstracts* vol. 62, No. 430c, (1965).
Angewandte Chemie, Band 98, Nr. 1, Jan. 1986, Seiten 96–97, VCH Verlagsgesellschaft mbH, Weinheim, DE; D. Seebach et al.: "Diund Trifluorosubstituierte Dilithium–Verbindungen fur die Organische Synthese" *Seite 97; Verbindungen 6–9*.
Journal of Pharmaceutical Sciences, Band 56, Nr. 8, Aug. 1967, Seiten 970–973, American Pharmaceutical Association, Washington, D.C. US; R. M. Pinder et al.: "Trifluoromethyl Analogs of Amphetamine and Norephedrine" *Seite 972, Rechte Spalte, Abschnitt 6*.

*Primary Examiner*—Richard L. Raymond
*Assistant Examiner*—John A. Sopp
*Attorney, Agent, or Firm*—Sprung Horn Kramer & Woods

[57] ABSTRACT

Fluorinated nitroalcohols of the formula (I)

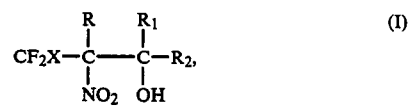

process for their preparation by reaction of fluoronitroalkane of the formula (II)

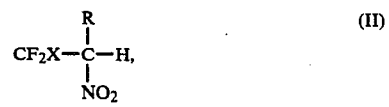

with a carbonyl compound of the formula (III)

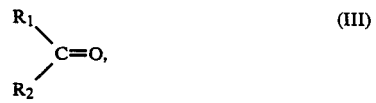

fluorinated aminoalcohols of the formula (IV)

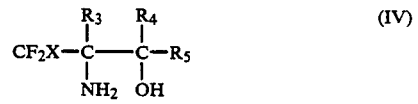

and a process for their preparation by hydrogenation of compounds of the formula (I).

2 Claims, No Drawings

FLUORINATED NITRO- AND AMINOALCOHOLS

The present invention relates to fluorinated nitroalcohols, fluorinated aminoalcohols and processes for the preparation of fluorinated nitro- and aminoalcohols.

The only compound which is known from the group of the $CF_3$-substituted aminoalcohols is 2-amino-3-hydroxy-3-phenyl-1,1,1-trifluoropropane, which can be prepared with poor yields in a 4-stage synthesis. This compound has a very weak blood pressure-raising action (see J. Pharm. Sciences 56, 971 (1967)).

Fluorinated nitroalcohols of the formula (I)

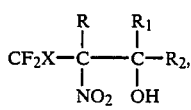

in which
X represents fluorine or hydrogen,
R represents hydrogen or $C_1$–$C_6$-alkyl,
$R_1$ and $R_2$, independently of one another, in each case represent hydrogen, optionally substituted $C_1$- to $C_6$-alkyl, optionally substituted $C_6$- to $C_{10}$-aryl or optionally substituted heteroaryl containing 5 to 7 ring atoms,
where
$R_1$ and $R_2$, together with the C atom to which they are bound, alternatively represent an optionally substituted, saturated $C_5$- to $C_7$-ring,
have now been found, in the R and S form and any mixtures of these forms in the cases in which $R_1$ and $R_2$ are identical or part of an unsubstituted or symmetrically substituted saturated $C_5$- to $C_7$-ring, and in the R,R, R,S, S,R and S,S form and any mixtures of two, three and all of these forms in the cases in which $R_1$ and $R_2$ are different or part of an asymmetrically substituted saturated $C_5$- to $C_7$-ring.

Suitable substituents on $C_1$- to $C_6$-alkyl, $C_6$- to $C_{10}$-aryl, heteroaryl containing 5 to 7 ring atoms and saturated $C_5$- to $C_7$-rings are, for example, nitro, halogen, $C_1$- to $C_4$-alkoxy and CN groups. Preferred halogens in this case are fluorine, chlorine and bromine, particularly preferred halogens are fluorine and chlorine. Preferred $C_1$- to $C_4$-alkoxy groups in this case are methoxy, ethoxy and propoxy groups. $C_1$- to $C_6$-alkyl and saturated $C_5$- to $C_7$-rings can also be substituted by optionally substituted aromatic groups. In this case, phenyl, p-nitrophenyl and 3,4-methylenedioxyphenyl groups are preferred. $C_6$- to $C_{10}$-aryl and heteroaryl containing 5 to 7 ring atoms can also be substituted by $C_1$- to $C_6$-alkyl groups. In this case, $C_1$- to $C_4$-alkyl groups, such as methyl, ethyl, propyl, n-butyl, iso-butyl and tert.-butyl, are preferred.

N and/or O atoms can, for example, be present in heteroaryl containing 5 to 7 ring atoms, such as in the pyrrole, imidazole, oxazole, pyrazole, pyrimidine, furan or pyridine ring system. Preferably, one N atom or one O atom is present, such as in the pyridine or furan ring system.

In formula (I), X preferably represents fluorine.

In formula (I), R particularly preferably represents hydrogen or methyl, $R_1$ particularly preferably represents hydrogen and $R_2$ particularly preferably represents $C_3$- to $C_6$-alkyl or phenyl, which optionally contain one of the substituents described above. $R_1$ and $R_2$, together with the C atom to which they are bound, also particularly preferably form an unsubstituted saturated $C_6$-ring.

Very particularly preferred individual compounds corresponding to the formula (I) are listed in Table 1.

TABLE 1

| X | R | $R_1$ | $R_2$ |
|---|---|---|---|
| F | H | H | phenyl |
| F | H | H | n-propyl |
| F | H | H | tert.-butyl |
| F | H | H | n-hexyl |
| F | H | H | p-nitrophenyl |
| F | H | H | 3,4-methylenedioxyphenyl |
| F | H | H | —$CH_2$—$CH_2$—phenyl |
| F | H | H | —CH—$CH_3$<br>　\|<br>　phenyl |
| F | H | —$(CH_2)_5$— | |
| F | $CH_3$ | H | n-Propyl |
| F | $CH_3$ | H | n-hexyl |
| F | $CH_3$ | H | —$CH_2$—$CH_2$—phenyl |
| H | H | H | phenyl |
| H | H | H | tert.-butyl |
| H | H | —$(CH_2)_5$— | |

In the cases in which $R_1$ and $R_2$ are indentical or part of an unsubstituted or symmetrically substituted saturated $C_5$- to $C_7$-ring, the compounds of the formula (I) possess an asymmetrical C atom. Such compounds can therefore arise in the R form, the S form and in any mixtures of these forms. In the cases in which $R_1$ and $R_2$ are different or part of an asymmetrically substituted, saturated $C_5$- to $C_7$-ring, the compounds of the formula (I) have two asymmetrical C atoms. Such compounds can therefore arise in the R,R, R,S, S,R and S,S form and in any mixtures of two, three and all of these forms.

The present invention relates to the compounds of the formula (I), in each case both in the individual forms (either R or S form or R,R, R,S, S,R or S,S form), and in any mixtures of either the R and S form or of the R,R, R,S, S,R and/or S,S form.

Mixtures which contain the R and S form of a compound of the formula (I) having an asymmetrical C atom can contain, for example, 30 to 70% by weight of the R form and the remainder up to 100% by weight of the S form. mixtures which contains the R,R, R,S, S,R and/or S,S form of a compound of the fdrmula (I) having two asymmetrical C atoms can contain two, three or all four of these forms. In such mixtures, for example, any first component (R,R, R,S, S,R or S,S form) can be present in a proportion of 1 to 70% by weight and a second or a second and third or a second, third and fourth component can be present as the remainder to 100%. Such mixtures preferably contain all four components, that is to say the R,R, R,S, S,R and S,S form of a compound of the formula (I) having two asymmetical C atoms, each of these components preferably being present in an amount between 15 and 35% by weight and the sum of all components giving 100% by weight.

Examples which may be mentioned of optically active forms of compounds of the formula (I) and mixtures containing them are: R,R-1,1,1-trifluoro-2-nitro-3-phenylpropan-3-ol, R,S-1,1,1,-trifluoro-2-nitro-3-phenyl-propan3-ol, S,R-1,1,1-trifluoro-2-nitro-3-phenyl-propan-3-ol, S,S-1,1,1-trifluoro-2-nitro-3-phenyl-propan-3-ol, and mixtures of all four of these individual forms, each individual form having a proportion of the total mixture of between 15 and 35% by weight and the sum of all four components giving 100% by weight, and also R-1-hydroxy-1-(2,2,2-trifluoro-1-nitro-ethyl)-cylcohexane, S-1-hydroxy-1-(2,2,2- triluoro-1-nitro-ethyl)-cyclohexane, and mixtures of these cyclohexanes, which contain 30 to 70% by weight of the R component and the S component as the remainder to 100% by weight.

The composition of a present mixture of optical isomers of a compdund of the formula (I) can be modified in a manner which is known per se. For example, if R represents hydrogen, the OH group on the neighbouring C atom can be protected, for example by conversion into the corresponding trimethylsilyl ether, subsequently carrying out a deprotonation, followed by a protonation, preferably at temperatures in the range −90° to −100° C., using glacial acetic acid, and finally cleaving the protecting group off again. When R represents $C_1$- to $C_6$-alkyl, the composition of a present mixture of optical isomers of a compound of the formula (I) can be altered, for example, by carrying out an oxidation and subsequently reducing. This can also be achieved using chromatographical methods, irrespective of the radicals R, $R_1$ and $R_2$. Pure optical isomers of compounds of the formula (I) can be obtained from mixtures of optical isomers, likewise in a manner which is known per se, for example by high-pressure liquid chromatography (HPLC).

Furthermore, a process for the preparation of fluorinated nitroalcohols of the formula (I)

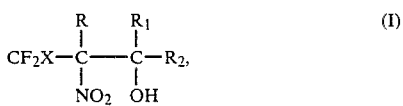

in which

X represents fluorine,

R represents hydrogen or $C_1$–$C_6$-alkyl, $R_1$ and $R_2$, independently of one another, in each case represent hydrogen, optionally substituted $C_1$- to $C_6$-alkyl, optionally substituted $C_6$- to $C_{10}$-aryl or optionally substituted heteroaryl containg 5 to 7 ring atoms, where $R_1$ and $R_2$, together with the C atom to which they are bound, alternatively represent an optionally subbstituted, saturated $C_5$- to $C_7$-ring, has been found which is characterized in that fluoronitroalkanes of the formula (II)

in which

X represents fluorine and

R has the meaning stated for formula (I), are reacted with carbonyl compounds of the formula (III)

$R_1$ and $R_2$ have the meaning stated for formula (I), in the presence of potassium fluoride or aluminum oxide.

In this process, according to the invention, for the preparation of fluorinated nitroalcohols of the formula (I), fluoronitroalkanes of the formula (II) can be employed, for example, which have been obtained according to DE-OS (German Published Specification) No. 3,305,201 or DE-OS (German Published Specification) No. 3,305,202. The use of fluoronitroalkanes of the formula (II) in which R represents hydrogen or methyl is preferred.

Of the carbonyl compounds of the formula (III), those are preferred in which $R_1$ and $R_2$ have the meanings which are stated in the description of the new fluorinated nitroalcohols of the formula (I) as being preferred for $R_1$ and $R_2$. Particularly preferred carbonyl compounds of the formula (III) are benzaldehyde, n-butyraldehyde, 2,2,2-trimethylacetaldehyde, n-heptanal, p-nitrobenzaldehyde, 3,4-methylenedioxybenzaldehyde, 3-phenylpropanal, 2-phenylpropanal and cyclohexanone.

The carbonyl compounds of the formula (III) are easily accessible, mostly commercially available products.

Although a compound of the formula (II) reacts with a compound of the formula (III) in the molar ratio of 1:1, one of these two reaction components is preferably employed in an excess, for example in the molar ratio of 2:1 to 1:2. Since the carbonyl compound of the formula (III) is frequently more easily accessible, it is, in general, advantageous, for reactions on an industrial scale, to employ the compounds of the formula (III) in an excess, for example in a molar ratio to the compound of the formula (II) of 1.2 to 2:1.

This process according to the invention is carried out in the presence of potassium fluoride or aluminum oxide. The potassium fluoride can here be employed in an industrial form or a chemically pure form, and may be anhydrous or water-containing. The potassium fluoride is preferably used in chemically pure, anhydrous form. The aluminum oxide can here be acidic, neutral or basic and of any activity. Conventional commercial basic aluminum oxide of activity stage I in the form of fine powder is preferably used. Potassium fluoride can be employed, for example, in amounts from 0.05 to 100 mol %, preferably 0.1 to 70 mol %, relative to the compound of the formula (II). Aluminum oxide can be employed, for example, in amounts from 0.1 to 500 mol %, preferably 10 to 200 mol %, relative to the compound of the formula (II).

Suitable temperatures for this process according to the invention are, for example, those between 0° C. and the boiling point (atmospheric pressure) of the lowest boiling component of the reaction mixture. This process according to the invention is particularly preferably and simply carried out at room temperature that is to say at 20° to 25° C. ambient temperture In general, this process according to the invention is carried out at atmospheric pressure. However, reduced and increased pressures and high pressures can also be used, for example those in the range from 0.5 bar to 15 kbar.

This process according to the invention can be carried out in the presence or in the absence of solvents. If solvents are to be employed, alcohols, for example, particularly isopropanol, can be used for these. The use of alcohols as solvents is in general advantageous when a fluoronitroalkane of the formula (II) with R=$C_1$- to $C_6$-alkyl and/or a carbonyl compound of the formula (III) with $R_1$ and/or $R_2$=optionally substituted $C_6$- to $C_{10}$-aryl or optionally substituted heteroaryl containing 5 to 7 ring atoms is employed and the process is carried out in the presence of potassium fluoride.

The mixture is advantageously stirred during this reaction according to the invention. However, the reaction can also frequently be brought to completion simply by allowing the appropriate batch to stand. The reaction time can be, for example, in the range from 30 minutes to 30 hours, preferably in the range from 20 to 25 hours.

The mixture which is present after this reaction according to the invention can be worked up, for example, as follows: firstly, solid components of the reaction mixture are separated, for example by filtration, and then relatively volatile components, if present, of the reaction mixture, for example solvent and/or unreacted fluorinated nitroalkane of the formula (II), are separated, which can occur, for example, by evaporation, if appropriate at reduced pressure. A non-water-miscible solvent, for example diethyl ether, and water are added, any unreacted carbonyl compound of the formula (III) present being able to be removed by means of the use of an aqueous $NaHSO_3$ solution in place of water. The mixture is then re-filtered, the middle phase of the solution is separated from the water phase, the solvent is removed from the middle phase of the solution, for example by evaporation, and the compound of the formula (I) is thus obtained. The compound of the formula (I) which has been isolated in this manner is sufficiently pure for many applications. If desired, it can be further purified, for example by fractional distillation, if appropriate at reduced pressure.

In general, the fluorinated nitroalcohols of the formula (I) are present as a mixture of the diastereomeric enantiomer pairs. The isomer distribution in such a mixture can be modified and the separation of individual isomers from such a mixture can be carried out as described above.

In addition, a further process for the preparation of fluorinated nitroalcohols of the formula (I)

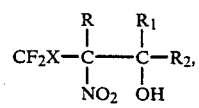

in which
X represents fluorine or hydrogen,
R represents hydrogen and
$R_1$ and $R_2$ has been found which is characterized in that fluoronitroalkanes of the formula (II)

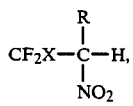

in which
X represents fluorine or hydrogen and
R represents hydrogen,
are initially reacted with a lithium alkyl compound at temperatures in the range $-80°$ to $-130°$ C. in the presence of an aprotic solvent and, if appropriate, in the presence of a cosolvent, and subsequently adding a carbonyl compound of the formula (III)

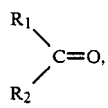

in which
$R_1$ and $R_2$ have the abovementioned meaning, to the reaction mixture at $-80°$ to $-130°$ C., subsequently warming to $-60°$ to $-80°$ C., then adding glacial acetic acid and an aprotic solvent at $-80°$ to $-130°$ C. and subsequently warming to a temperature above $-20°$ C.

The preferred and particularly preferred meanings of $R_1$ and $R_2$ in the formulae (I), (II) and (III) are as stated above.

Suitable aprotic solvents for this process according to the invention are, for example, cyclic ethers. Tetrahydrofuran is preferred. The reaction with a lithium alkyl compound is preferably carried out in the presence of a cosolvent. Examples of suitable cosolvents are cyclic urea derivatives, such as N,N-dimethylpropyleneurea and N,N-dimethylethyleneurea, and also hexamethylphosphoric triamide. N,N-Dimethylpropyleneurea is preferred.

Examples of suitable lithium alkyl compounds are those in which the alkyl radical has 1 to 4 C atoms and is straight-chained. n-Butyllithium is preferred.

The range from $-90°$ to $-100°$ C. is preferred within the temperature range from $-80°$ to $130°$ C., and the range from $-65°$ to $-75°$ C. is preferred within the temperature range from $-60°$ to $-80°$ C. The subsequent warming to a temperature above $-20°$ C. can occur, for example, to a temperature up to $+50°$ C. Preferred final temperatures are those between $+5°$ and $+20°$ C.

500 to 5000 ml of an aprotic solvent, 500 to 2000 ml of a cosolvent, 1.5 to 2.5 moles of lithium alkyl compound, 0.8 to 1.5 moles of carbonyl compound of the formula (III) and 1.5 to 2.5 moles of glacial acetic acid can be employed here, for example, per mole of a fluorinated nitroalkane of the formula (II).

The mixture present after warming to a temperature above $-20°$ C. can be worked up, for example, by shaking this mixture in a diethyl ether/water mixture, separating off the ether phase, washing with plenty of water (to remove any cosolvent present), then evaporating the ether phase and thus obtaining the fluorinated nitroalcohol of the formula (I).

Furthermore, new fluorinated aminoalcohols of the formula (IV) have been found

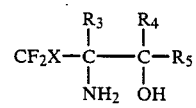

in which
X represents fluorine or hydrogen,
$R_3$ represents hydrogen or $C_1$- to $C_6$-alkyl,
$R_4$ and $R_5$, independently of one another, in each case represent hydrogen, optionally substituted $C_1$- to $C_6$-alkyl, optionally substituted $C_6$- to $C_{10}$-aryl or optionally substituted heteroaryl containing 5 to 7 ring atoms,
where the combination of $X=F/R_3=H/R_4=H/R_5=$unsubstituted phenyl is excluded, and where R$_4$ and R$_5$, together with the C atom to which they are bound, alternatively represent an optionally substituted, saturated C$_5$- to C$_7$-ring,
in the R and S form and any mixtures of these forms in the cases in which R$_4$ and R$_5$ are identical or part of an unsubstituted or symmetrically substituted saturated C$_5$- to C$_7$-ring, and in the R,R, R,S, S,R and S,S form and any mixtures of two, three or all four of these forms in cases in which R$_4$ and R$_5$ are different or part of an asymmetrically substituted C$_5$- to C$_7$-ring.

Examples of suitable substituents on C$_1$- to C$_6$alkyl, C$_6$- to C$_{10}$-aryl, heteroaryl containing 5 to 7 ring atoms and saturated C$_5$- to C$_7$-rings are nitro, halogen C$_1$- to C$_4$-alkoxy groups and CN groups. Preferred halogens here are fluorine, chlorine and bromine, and particularly preferred halogens are fluorine and chlorine. Preferred C$_1$- to C$_4$-alkoxy groups here are methoxy, ethoxy and propoxy groups. C$_1$- to C$_6$-alkyl and saturated C$_5$- to C$_7$-rings can also be substituted by optionally substituted aromatic groups. Phenyl groups, p-nitrophenyl groups and 3,4-methylenedioxyphenyl groups are preferred here. C$_6$- to C$_{10}$-aryl and heteroaryl containing 5 to 7 ring atoms can also be substituted by C$_1$- to C$_6$-alkyl groups. C$_1$- to C$_4$-alkyl groups, such as methyl, ethyl, propyl, n-butyl, iso-butyl and tert.-butyl, are preferred here.

N and/or O atoms can be present, for example, in heteroaryl containing 5 to 7 ring atoms. One N atom or one O atom is preferably present, such as in the pyridine or furan ring system.

In formula (IV), R$_3$ particularly preferably represents hydrogen or methyl, R$_4$ particularly preferably represents hydrogen and R$_5$ particularly preferably represents C$_3$- to C$_6$-alkyl and, if R$_3$ and/or R$_4$ is not hydrogen, alternatively represents phenyl. Very particularly preferred individual compounds correspond to the formula (IV) with X=fluorine, and are listed in Table 2.

TABLE 2

| R$_3$ | R$_4$ | R$_5$ |
|---|---|---|
| H | H | n-propyl |
| H | H | tert.-butyl |
| H | H | n-hexyl |
| H | H | p-nitrophenyl |
| H | H | 3,4-methylenedioxyphenyl |
| H | H | —CH$_2$—CH$_2$—phenyl |
| H | H | —CH—CH$_3$<br>    \|<br>   phenyl |
| H | —(CH$_2$)$_5$— | |
| CH$_3$ | H | n-propyl |
| CH$_3$ | H | n-hexyl |
| CH$_3$ | H | —CH$_2$—CH$_2$—phenyl |

The compounds of the formula (IV) also have an asymmetrical C atom in the cases in which R$_4$ and R$_5$ are identical or part of an unsubstituted or symmetrically substituted saturated C$_5$- to C$_7$-ring. Such compounds can therefore arise in the R form, the S form, and in any mixtures of these forms. In the cases in which R$_4$ and R$_5$ are different or part of an asymmetrically substituted saturated C$_5$- to C$_7$-ring, the compounds of the formula (IV) have two asymmetrical C atoms. Such compounds can therefore arise in the R,R, R,S, S,R and S,S form, and in any mixtures of two, three and all of these forms.

The present invention relates to the compounds of the formula (IV), in each case both in the individual forms (either R or S form or R,R, R,S, S,R or S,S form) and also in any mixtures of either the R and S form or of the R,R, R,S, S,R and/or S,S form.

Mixtures which contain the R and S form of a compound of the formula (IV) having an asymmetrical C atom can contain, for example, 30 to 70% by weight of the R form and the S form as the remainder up to 100% by weight. Mixtures which contain the R,R, R,S, S,R and/or S,S form of a compound of the formula (IV) having two asymmetrical C atoms can contain two, three or all four of these forms. In such mixtures, for example, any first component (R,R, R,S, S,R or S,S form) can be present in a proportion of 1 to 70% by weight and a second or a second and third or a second, third and fourth component can be present as the remainder up to 100%. Such mixtures preferably contain all four components, that is to say the R,R, R,S, S,R and S,S form of a compound of the formula (IV) having two asymmetrical C atoms, each of these components preferably being present in an amount between 15 and 35% by weight and the sum of all components giving 100% by weight.

Examples of optically active forms of compounds of the formula (IV), and mixtures containing them, which may be mentioned are: R,R-1,1,1-trifluoro-2-methyl-2-amino-3-phenyl-propan-3-ol, R,S-1,1,1-trifluoro-2-methyl-2-amino-3-phenyl-propan-3-ol, S,R-1,1,1-trifluoro-2-methyl-2-amino-3-phenyl-propan-3-ol, S,S-1,1,1-trifluoro-2-methyl-2-amino-3-phenyl-propan-3-ol and mixtures of all four of these individual forms, each individual form having a proportion of the total mixture between 15 and 35% by weight and the sum of all four components giving 100% by weight, and also R-1-hydroxy-1-(2,2,2-trifluoro-1-amino-ethyl)cyclohexane, S-1-hydroxy-1-(2,2,2-trifluoro-1-amino-ethyl)cyclohexane, and mixtures of these cyclohexanes which contain 30 to 70% by weight of the R component and the S component as the remainder up to 100% by weight.

The composition of a present mixture of optical isomers of a compound of the formula (IV) can be modified in a manner which is known per se and pure optical isomers of compounds of the formula (IV) can be obtained from mixtures of optical isomers, likewise in a manner which is known per se, for example by high-pressure liquid chromatography (HPLC) or by fractional crystallization.

Furthermore, a process for the preparation of fluorinated aminoalcohols of the formula (V)

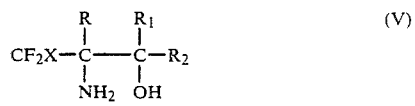

in which

X represents fluorine or hydrogen,

R, R$_1$ and R$_2$, independently of one another, in each case represent hydrogen, optionally substituted C$_1$- to C$_6$-alkyl, optionally substituted C$_6$- to C$_{10}$-aryl or optionally substituted heteroaryl containing 5 to 7 ring atoms, where R$_1$ and R$_2$, together with the C atom to which they are bound, alternatively represents an optionally substituted, saturated C$_5$- to C$_7$-ring, has been found which is characterized in that fluorinated nitroalcohols of the formula (I)

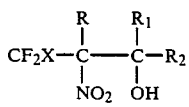

in which

X represents fluorine or hydrogen,

R, $R_1$ and $R_2$ have the meaning stated for formula (V), are hydrogenated.

The starting materials, the fluorinated nitroalcohols of the formula (I), for this process can be obtained, as described above, for example by reaction of fluorinated nitroalkanes of the formula (II)

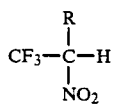

in which

R has the meaning stated for formula (V), with carbonyl compounds of the formula (III)

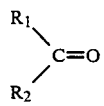

in which $R_1$ and $R_2$ have the meaning stated for formula (V), in the presence of potassium fluoride or aluminium oxide.

The hydrogenation according to the invention can be carried out, for example, catalytically using hydrogen, or by reaction with metal hydrides.

Such a catalytic hydrogenation using hydrogen can be carried out in the presence or in the absence of solvents. In general, it is advantageous to work in the presence of a solvent, since better control of the hydrogenation, which proceeds exothermically, is then possible.

Examples of suitable solvents are inert organic solvents. For example, alcohols, such as methanol, ethanol, ethylene glycol and diethylene glycol, ethers, such as dixane, tetrahydrofuran, ethylene glycol monomethyl ether, ethylene glycol monoethyl ether, ethylene glycol dimethyl ether, diethylene glycol monoethyl ether and diethylene glycol dimethyl ether, saturated hydrocarbons, such as cyclohexane, or esters, such as ethyl acetate, are suitable.

Methanol or ethanol is preferably employed as solvent. In this case, it is in general possible to separate the solvent from the hydrogenation product easily by distillation.

The catalytic hydrogenation, according to the invention, using hydrogen can be carried out in reaction apparatuses which are suitable for hydrogenations at atmospheric pressure and/or hydrogenations under pressure. Suitable materials for the reaction apparatuses are, for example, glass, enamels, steel or stainless steel.

The hydrogen pressure under which the hydrogenation is carried out can vary within wide limits. A pressure from 1 to 30 bar is preferred, and a pressure from 5 to 20 bar is particularly preferred.

The reaction temperature can likewise be varied within wide limits and can be, for example, between 0° and 120° C. Temperatures between 10° and 80° C. are particularly preferred, and those between 20° and 60° C. are very particularly preferred.

The amount of hydrogen can likewise be varied within wide limits. At least 3 moles of hydrogen are preferably employed per mol of the compound of the formula (I). If further reactions with hydrogen are, in principle, possible, for example the hydrogenation of a further nitro group present, and if such further reactions with hydrogen are undesired, it is advantageous to avoid relatively large excesses of hydrogen, for example to employ more than 8 moles of hydrogen per mol of the compound of the formula (I).

The reaction time required for the catalytic hydrogenation, according to the invention, using hydrogen is dependent on the reaction rate, the partial pressure of hydrogen, the intensity of the mixing of the reaction mixture and on the activity and concentration of the hydrogenation catalyst. In general, the necessary reaction time is in the range from 15 minutes to several hours.

Suitable catalysts for the catalytic hydrogenation, according to the invention, using hydrogen are, for example, those which comprise or contain metals and/or compounds of elements of the 8th subgroup of the Mendelev periodic system of the elements. The metals ruthenium, rhodium, palladium, platinum, cobalt and nickel, and their compounds, are preferred here. In the case of the metal compounds, these can be, for example, oxides, hydroxides and/or oxyhydrates. In addition, further metals, for example copper, vanadium, molybdenum, chromium and/or manaanese, and also compounds of these metals, can be present.

Such hydrogenation catalysts can exclusively or mainly comprise the hydrogen-transferring substances described above, but these can also be applied to support materials. Examples of suitable support materials for the hydrogen-transferring substances are inorganic materials, such as Kieselguhr, silicic acid, aluminum oxides, alkali metal and alkaline earth metal silicates, aluminum silicates, montmorillonite, zeolites, spinels, dolomites, kaolin, magnesium silicates, zirconium oxide, zinc oxide, calcium carbonate, silicon carbide, aluminum phosphate, boron phosphate, asbestos, activated charcoal or barium sulphate, but also organic materials, for example naturally occurring or synthetic compounds having high molecular weight, such as silk, polyamides, polystyrenes, cellulose or polyurethanes. Inorganic support materials are preferred. The support material can be present, for example, in the form of spheres, strands, threads, cylinders, polygons or in powder form.

Such support catalysts can contain, in general, 0.5 to 50% by weight, preferably 1 to 10% by weight, of the hydrogen-transferring substance, relative to the total weight of the support catalyst. The hydrogen-transferring substance here can be homogeneously distributed in the support material. However, catalysts in whose external layer or on whose surface the hydrogen-transferring substance is deposited are preferred. The preparation and shaping of catalysts which can be used for the catalytic hydrogenation, according to the invention, using hydrogen can occur in a manner which is known per se (see, for example, Houben-Weyl, Methoden der organischen Chemie [Methods of Organic Chemistry], volume VI, 1c, part I, pages 16 to 26, Georg Thieme Verlag, Stuttgart, 1980).

Preferred support catalysts are ruthenium on charcoal, ruthenium on aluminum oxide, rhodium on charcoal, rhodium on aluminum oxide, pallidium on calcium carbonate, dium on aluminium oxide, palladium on calcium carbonate, palladium on barium sulphate, palladium on silicic acid, platinum on charcoal and platinum on aluminum oxide.

Preferred hydrogenation catalysts which exclusively or mainly comprise hydrogen-transferring substance are, for example, oxidic catalysts, such as palladium oxide, platinum oxide, ruthenium oxide and/or Nishimura rhodium oxide/platinum oxide, furthermore black catalysts, such as palladium black, platinum black and rhodium black, which are prepared by reduction of appropriate metal salts or metal salt mixtures using, for example, alkali metal hydrides, alkali metal borohydrides, metal alkyls, hydrazine, formaldehyde, hydrogen or relatively eletropositive metals.

Particularly preferred catalysts for the catalytic hydrogenation, according to the invention, using hydrogen are palladium on charcoal, palladium on aluminum oxide, palladium on silicic acid and palladium on calcium carbonate.

Raney-type skeleton catalysts can also be employed for the catalytic hydrogenation, according to the invention, using hydrogen, Raney nickel being preferred. However, it should be ensured in this case that only Raney nickel which has been carefully washed until neutral is used, since undesired side-reactions can otherwise occur.

The catalyst for the catalytic hydrogenation, according to the invention, using hydrogen can be employed, for example, in amounts from 0.1 to 150% by weight of hydrogen-transferring substance, relative to the compound of the formula (I). For batches on an industrial scale, preferably 0.1 to 20% by weight, particularly preferably 0.2 to 5% by weight, of hydrogen-transferring substance are employed, relative to the compound of the formula (I).

Mixtures of two or more of the hydrogenation catalysts mentioned can also be used to carry out the catalytic hydrogenation, according to the invention, using hydrogen.

The catalytic activity of the hydrogenation catalysts is, in general, essentially maintained when the process according to the invention is carried out, so that these catalysts can be repeatedly employed in batch operations and can remain in use for a relatively long period in continuous operations.

The catalytic hydrogenation, according to the invention, using hydrogen can be carried out, for example, as follows in a simple batch embodiment: an autoclave which is fitted with a stirrer or mixer and the temperature of which can be regulated is charged with the compound of the formula (I) to be employed, the hydrogenation catalyst and a solvent. Hydrogen is then introduced to the desired pressure and the mixture is heated to the desired reaction temperature with intensive mixing. The course of the reaction can easily be followed by measuring the hydrogen consumption. When the theoretical amount of hydrogen has been taken up, the hydrogenation can be stopped, for example by cooling, stopping the mixing, releasing the pressure and/or removal of the hydrogen atmosphere. The reaction mixture can be worked up, for example, by first filtering off the catalyst, then removing the solvent by distillation and purifying the reaction products which remain, if appropriate by distillation or crystallization. The catalytic hydrogenation, according to the invention, using hydrogen can alternatively be carried out continuously.

However, the hydrogenation according to the invention can also be carried out using metal hydrides. Suitable metal hydrides for this are, for example, alkali metal and/or alkaline earth metal hydrides, including those containing further metals. A preferred metal hydride is lithium aluminum hydride. It is generally necessary to protect the OH group of the compound of the formula (I) before the reaction of the compound of the formula (I) with metal hydrides. This can be carried out, for example, in a manner which is known per se, by formation of the corresponding silyl ether and THP or alkoxyethyl derivatives, the trimethylsilyl ether and the t.-butyl-dimethylsilyl ether being particularly suitable.

The metal hydride is preferably employed in a stoichiometrical excess, relative to the compound of the formula (I).

The hydrogenation, according to the invention, using metal hydrides is preferably carried out in an inert solvent. Suitable solvents here are, for example, ethers. Diethyl ether is preferred here.

For such hydrogenations using metal hydrides, temperatures between 0° C. and the boiling point of the solvent, for example, are suitable. When diethyl ether is used as solvent, the hydrogenation is preferably carried out in refluxing diethyl ether.

The new fluorinated aminoalcohols of the formula (IV) are pharmaceuticals and plant-protecting agents, particularly insecticides.

The new fluorinated aminoalcohols of the formula (IV) and the known 2-amino-3-hydroxy-3-phenyl-1,1,1-trifluoro-propane can be prepared in a simple manner and in good yields according to the invention.

The new fluorinated nitroalcohols of the formula (I) can be used, as described, as intermediates for the preparation of fluorinated aminoalcohols of the formula (V).

EXAMPLES

I. General procedures

A. General procedures for the preparation of nitroalcohols of the formula (1) using potassium fluoride and isopropanol.

184 mmol of a fluoronitroalkane were dissolved in 100 ml of isopropanol in a 250 ml round-bottomed flask, 78.6 mmol of a carbonyl compound of the general formula (III) and 6.8 mmol of KF were added, and the mixture was stirred for 24 hours at 20° C. under inert gas (argon). For working up, the reaction mixture was filtered through a frit, charged with Celite ®. The Celite was rinsed with 100 ml of $CH_2Cl_2$, and the filtrate was evaporated on a rotary evaporator at a bath temperature of 45° C.

The crude product was dissolved in 200 ml of diethyl ether, the same amount of saturated $NaHSO_3$ solution was added and the mixture was stirred for 24 hours at 20° C. The mixture was subsequently filtered again through a frit charged with Celite ® and rinsed with 100 ml of diethyl ether, and the phases were separated. The aqeous phase was extracted once with 100 ml of diethyl ether, and the combined organic phases were washed 3 times with 100 ml of saturated sodium chloride solution in each case, dried over magnesium sulphate and evaporated on a rotary evaporator.

B. General procedure for the preparation of nitroalcohols of the formula (I) using KF, without isopropanol 92 mmol of a fluoronitroalkane, 40 mmol of a carbonyl compound of the formula (III) and 3.4 mmol of KF were placed in a 50 ml flask and stirred for 24 hours under inert gas (argon). The reaction mixture was then filtered through a frit charged with Cel rinsed with 100 ml of $CH_2Cl_2$, and evaporated on a rotary evaporator at a bath temperature of 45° C.

The crude product was dissolved in 100 ml of diethyl ether, treated with the same amount of saturated $NaHSO_3$ solution and stirred for 24 hours at 20° C. The mixture was subsequently again filtered through a frit, which was charged with Celite ®, and the phases were separated. The aqueous phase was extracted once with 50 ml of diethyl ether, and the combined organic phases were washed 3 times with 50 ml of saturated sodium chloride solution in each case, dried over magnesium sulphate and evaporated on a rotary evaporator.

C. General procedure for the preparation of nitroalcohols of the formula (I) using $Al_2O_3$.

25 mmol of a fluoronitroalkane were placed in a 50 ml flask under inert gas (argon) and cooled using an ice bath, the equimolar amount of a carbonyl compound of the formula (III) was added and 5 g of $Al_2O_3$ (neutral, activity stage I) was added with stirring. After 5 minutes, the ice bath was removed, and the mixture was stirred for 1 hour and then allowed to stand for 24 hours at 20° C. For working up, the reaction product was filtered through a frit charged with Celite ® and rinsed with 50 ml of $CH_2Cl_2$, and the filtrate was evaporated on a rotary evaporator.

The crude product was dissolved in 100 ml of diethyl ether, treated with the same amount of saturated $NaHSO_3$ solution and stirred for 24 hours at 20° C. The mixture was then filtered through a frit, charged with Celite ®, the phases were separated, the aqueous phase was extracted once with 50 ml of diethyl ether, and the combined organic phases were washed 3 times with 50 ml of saturated sodium chloride solution in each case, dried over magnesium sulphate and evaporated on a rotary evaporator.

D. General procedure for the preparation of nitroalcohols using lithium alkyl compounds 10 mmol of a fluoronitroalkane were initially introduced in a 100 ml flask with a side neck, which was sealed with a serum stopper, and a ground joint provided with a three-way tap, and 45 ml of absolute THF were added, followed by 15 ml of absolute N,N-dimethylpropyleneurea. The internal temperature was reduced to −100° to −110° C. using a cooling bath (methanol/liquid nitrogen), with stirring, and 22.4 mmol of n-butyl-lithium (13.0 ml of a 1.59 molar solution in n-hexane) were added dropwise at such a rate that the internal temperature did not exceed −90° C. The mixture was stirred for 15–20 minutes. 10 mmol of a carbonyl compound of the formula (III) were then added at −95° C. (in the case of carbonyl compounds which are crystalline at room temperature, in the form of a solution in 10 ml of THF), ensuring that the temperature did not exceed −90° C. The mixture was subsequently allowed to warm to −80° to −75° C. within 45 minutes, kept at this temperature for a further 45 minutes and then cooled again to −100° to −110° C. A solution of 3.5 ml of glacial acetic acid (61 mmol) and 3 ml of THF was added dropwise to the reaction mixture thus cooled at such a rate that the internal temperature did not rise above −90° C. The mixture was then allowed to warm to −80°−−70° C. within one hour, the cooling bath was removed and the mixture was stirred for a further 30 minutes at an external temperature of 20° C., the internal temperature increasing to +5°−+10° C.

For working up, the reaction mixture was poured into a mixture of 75 ml of water and 75 ml of diethyl ether, the phases were separated, the aqueous phase was extracted once with 75 ml of diethyl ether, and the combined organic phases were washed 8 times with 75 ml of water in each case, dried over magnesium sulphate and evaporated on the rotary evaporator.

The product thus obtained was dissolved in 50 ml of diethyl ether, treated with the same amount of saturated $NaHSO_3$ solution and stirred for 24 hours at 20° C. The mixture was subsequently filtered through a frit, charged with Celite ®, the phases were separated, the aqueous phase was extracted once with 50 ml of diethyl ether, the combined organic phases were washed 3 times with saturated sodium chloride solution and dried over magnesium sulphate, and the volatile components were stripped off on a rotary evaporator.

E. General procedure for the catalytic hydrogenation of fluorinated nitroalcohols of the formula (I) to form fluorinated aminoalcohols of the formula (IV).

5 g of Raney nickel alloy were slurried in 50 ml of water in an Erlenmeyer flask and 8 g of sodium hydroxide were added in portions. The mixture was then warmed for a further 1 hour at 70° to 80° C. in a waterbath, subsequently washed until neutral with 50 ml portions of water and subsequently washed with ethanol until free of water. The active nickel thus obtained was rinsed in a 100 ml autoclave using 50 ml of ethanol, a solution of 2 g of the appropriate fluorinated nitroalcohol of the formula (I) in 50 ml of ethanol was added to this, a pressure of 25 to 30 bar of hydrogen was introduced and the mixture was hydrogenated for 24 hours at 50° C.

The contents of the autoclave were subsequently filtered through a frit, charged with Celite ®, rinsed with 50 ml of ethanol and evaporated on a rotary evaporator.

The product thus obtained was dissolved in 50 ml of diethyl ether, extracted 3 times with 50 ml of 10% strength aqueous hydrochloric acid in each case, the combined aqueous, hydrochloric acid phases were washed once with 50 ml of diethyl ether, and subsequently treated with solid sodium hydroxide with ice cooling until the solution was strongly basic. The mixture was then extracted 3 times with 50 ml of diethyl ether in each case, the combined organic phases were washed twice with 50 ml of saturated sodium chloride solution in each case and dried over magnesium sulphate, and the volatile components were stripped off on a rotary evaporator.

The aminoalcohol thus obtained was distilled and characterized as oxalate.

II. Exemplary embodiments
EXAMPLES 1 to 23 the structures stated. The index numbers for b.p. specify the pressure (in torr) in each case.

The diastereomeric ratio was determined from the

TABLE 3

| Example No. | Reaction product of the formula (I) | | | | General procedure | Yield in % crude (purified) | Melting (m.p.) or boiling point (b.p.) in °C. | | Diastereomeric ratio |
|---|---|---|---|---|---|---|---|---|---|
| | X | R | $R_1$ | $R_2$ | | | | | |
| 1 | F | H | H | Phenyl | A | (22) | $Kp_{0.6}$: | 80–85 | — |
| 2 | F | H | H | Phenyl | B | 10 | $Kp_{0.6}$: | 80–85 | — |
| 3 | F | H | H | Phenyl | C | 9 | $Kp_{0.6}$: | 80–85 | — |
| 4 | F | H | H | Phenyl | D | (39) | $Kp_{0.6}$: | 80–85 | 2:1 |
| 5 | F | H | H | n-Propyl | A | 71 | $Kp_{12}$: | 55–65 | — |
| 6 | F | H | H | n-Propyl | B | 73 | $Kp_{12}$: | 55–65 | — |
| 7 | F | H | H | n-Propyl | C | (50) | $Kp_{12}$: | 55–65 | 3:1 |
| 8 | F | H | H | t-Butyl | D | (59) | $Kp_{12}$: | 70–80 | 2:1 |
| 9 | F | H | H | n-Hexyl | A | 65 | $Kp_{12}$: | 120–130 | — |
| 10 | F | H | H | n-Hexyl | B | (60) | $Kp_{12}$: | 120–130 | 2:1 |
| 11 | F | H | H | p-NO$_2$phenyl | D | 53 | Fp: | 77.8–81.6 | 3:1 |
| 12 | F | H | H | 3,4-Methylendi-oxyphenyl | D | 40 | — | | 2.5:1 |
| 13 | F | H | H | —(CH$_2$)$_2$—Phenyl | B | 83 | $Kp_{12}$: | 145–150 | 2.5:1 |
| 14 | F | H | H | —CH—CH$_3$<br>\|<br>Phenyl | B | 46 | $Kp_{0.02}$: | 80 | 2:1.5:3:1 |
| 15 | F | H | —(CH$_2$)$_5$— | | D | 59 | $Kp_{12}$: | 95 | — |
| 16 | F | CH$_3$ | H | n-Propyl | A | (51) | $Kp_{12}$: | 80–90 | — |
| 17 | F | CH$_3$ | H | n-Propyl | B | 35 | $Kp_{12}$: | 80–90 | 1.5:1 |
| 18 | F | CH$_3$ | H | n-Propyl | C | (25) | $Kp_{12}$: | 80–90 | — |
| 19 | F | CH$_3$ | H | n-Hexyl | A | (49) | $Kp_2$: | 80–90 | 2:1 |
| 20 | F | CH$_3$ | H | —(CH$_2$)$_2$—Phenyl | B | 40 | $Kp_{0.06}$: | 95–100 | 2:1 |
| 21 | H | H | H | Phenyl | D | (12) | $Kp_{0.8}$: | 90–100 | 2:1 |
| 22 | H | H | H | t.-Butyl | D | 40 | $Kp_{12}$: | 95–105 | — |
| 23 | H | H | —(CH$_2$)$_5$— | | D | 60 | $Kp_{12}$: | 115–120 | — |

Explanatory notes on Table 3

The reaction product stated in each case was obtained by reaction of a nitroalkane of the formula (II), with X and R as stated in the case of the reaction product, with a carbonyl compound of the formula (III), with $R_1$ as stated in the reaction product and $R_2$=H. The exception here is Example 23, in the case of which cyclohexanone was employed as carbonyl compound.

The yields of crude product are weights after removal of the solvent and, in all cases, relate to the amount of carbonyl compound employed. The yields of purified product relate to a product which was distilled once (bulb tube oven).

All products display the OH bands (broad, 3500 cm$^{-1}$) and NO$_2$ bands (sharp, 1570 cm$^{-1}$) which are characteristic for nitroalcohols, and also intensive CF bands between 1140 and 1260 cm$^{-1}$ in the infra-red spectrum (film). The $^1$H and $^{13}$C NMR spectra confirm the structures stated. The index numbers for b.p. specify the pressure (in torr) in each case.

The diastereomeric ratio was determined from the $^{13}$C NMR spectrum.

EXAMPLES 24 to 30

TABLE 4

| Example No. | Reaction product of the formula (IV) | | | | Yield in % | Melting (m.p.) or boiling point (b.p.) in °C.) | | Melting point of the corresponding diamino monooxalate in °C. |
|---|---|---|---|---|---|---|---|---|
| | X | $R_3$ | $R_4$ | $R_5$ | | | | |
| 24 | F | H | H | n-Propyl | 52 | $Kp_{12}$: | 70–75 | 153.6–154.6 |
| 25 | F | H | H | n-Hexyl | 77 | $Kp_{12}$: | 115 | 158.5–159 |
| 26 | F | H | H | —(CH$_2$)$_2$—Phenyl | 79 | $Kp_{12}$:<br>Fp: | 135–145<br>40–50 | — |
| 27 | F | H | H | —CH—CH$_3$<br>\|<br>Phenyl | 83 | $Kp_{0.01}$:<br>Fp: | 70–75<br>131–132 | 157–161 |
| 28 | F | CH$_3$ | H | n-Propyl | 5 | — | | — |
| 29 | F | CH$_3$ | H | n-Hexyl | 22 | $Kp_2$: | 90 | — |
| 30 | F | CH$_3$ | H | —(CH$_2$)$_2$—Phenyl | 53.5 | $Kp_{0.8}$: | 90–100 | 158–160.6 |

Explanatory notes on Table 4

The reaction product stated in each case was obtained by hydrogenation of the appropriate fluorinated nitroalcohol in each case following the general procedure E.

The yields relate to distilled products.

The diastereomeric ratio of the aminoalcohols obtained by distillation essentially corresponds to that of the nitroalcohols employed.

In the IR spectra (film) of the liquid reaction products, a broad, irregular band appears in each case, in the OH/NH$_2$ region (3400 cm$^{-1}$) and the CF bands at 1130 to 1260 cm$^{-1}$, only broad bands of lower intensity lie between them, apart from in the case of compounds which contain aryl groups.

The $^1$H and $^{13}$C NMR spectra confirm the structures stated.

The index numbers in the case of b.p. specify the pressure (in torr) in each case.

The melting point of the monoamino monooxalate was determined in Example 30.

What is claimed is:

1. A fluorinated nitroalcohol of the formula

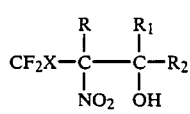

wherein said nitroalcohol is represented by the following table:

| X | R | R$_1$ | R$_2$ |
|---|---|---|---|
| F | H | H | phenyl |
| F | H | H | n-propyl |
| F | H | H | tert.-butyl |
| F | H | H | n-hexyl |
| F | H | H | p-nitrophenyl |
| F | H | H | 3,4-methylenedioxyphenyl |
| F | H | H | —CH$_2$—CH$_2$—phenyl |
| F | H | H | —CH—CH$_3$<br>\|<br>phenyl |
| F | H | —(CH$_2$)$_5$— | |
| F | CH$_3$ | H | n-Propyl |
| F | CH$_3$ | H | n-hexyl |
| F | CH$_3$ | H | —CH$_2$—CH$_2$—phenyl |
| H | H | H | phenyl |
| H | H | H | tert.-butyl |
| H | H | —(CH$_2$)$_5$— | |

2. A fluorinated nitroalcohol of the formula

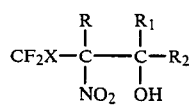

in which
X represents fluorine,
R represents hydrogen or methyl,
R$_1$ represents hydrogen and
R$_2$ represents C$_3$- to C$_6$-alkyl or phenyl or R$_1$ and R$_2$, together with the C atom to which they are attached, form an unsubstituted saturated C$_6$-ring.

* * * * *

UNITED STATES PATENT AND TRADEMARK OFFICE
CERTIFICATE OF CORRECTION

PATENT NO. : 4,778,935
DATED : Oct. 18, 1988
INVENTOR(S) : Beck et al.

It is certified that error appears in the above-identified patent and that said Letters Patent is hereby corrected as shown below:

| | |
|---|---|
| Col. 1, line 41 | Correct spelling of --heteroaryl-- |
| Col. 2, line 46 | Correct spelling of --Mixtures-- |
| Col. 2, line 47 | Correct spelling of --formula-- |
| Col. 3, line 2 | Correct spelling of --cyclohexane-- |
| Col. 3, line 48 | Correct spelling of --substituted-- |
| Col. 3, line 66 | Insert --in which-- after formula |
| Col. 5, line 52 | Insert --have the abovementioned meaning,-- after "$R_2$" |
| Col. 8, line 58 | Insert --R represents hydrogen or $C_1$- to $C_6$-alkyl,-- and delete "R," |
| Col. 9, line 46 | Correct spelling of --dioxane-- |
| Col. 13, line 9 | Delete "Cel" and substitute --Celite®,-- |
| Col. 13, line 10 | Delete "12" and substitute --2-- |

Signed and Sealed this

Eighth Day of August, 1989

Attest:

DONALD J. QUIGG

*Attesting Officer*   *Commissioner of Patents and Trademarks*